(12) United States Patent
Fang

(10) Patent No.: US 9,314,299 B2
(45) Date of Patent: Apr. 19, 2016

(54) FLOWER CATHETER FOR MAPPING AND ABLATING VEINOUS AND OTHER TUBULAR LOCATIONS

(75) Inventor: Itzhak Fang, Irvine, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 13/425,895

(22) Filed: Mar. 21, 2012

(65) Prior Publication Data

US 2013/0253504 A1 Sep. 26, 2013

(51) Int. Cl.
*A61B 5/042* (2006.01)
*A61B 18/14* (2006.01)
*A61B 17/00* (2006.01)
*A61B 18/00* (2006.01)

(52) U.S. Cl.
CPC ........... *A61B 18/1492* (2013.01); *A61B 5/0422* (2013.01); *A61B 2017/00867* (2013.01); *A61B 2018/00357* (2013.01); *A61B 2018/00577* (2013.01); *A61B 2018/00839* (2013.01); *A61B 2018/1467* (2013.01); *A61B 2218/002* (2013.01)

(58) Field of Classification Search
CPC .................... A61B 5/0422; A61B 18/1492
USPC ...................... 600/374, 381; 606/41
See application file for complete search history.

(56) References Cited

U.S. PATENT DOCUMENTS

| | | | |
|---|---|---|---|
| 3,769,984 A | 11/1973 | Muench | |
| 3,995,623 A | 12/1976 | Blake et al. | |
| 4,172,451 A | 10/1979 | Kline | |
| 4,444,195 A | 4/1984 | Gold | |
| 4,522,212 A | 6/1985 | Gelinas et al. | |
| 4,592,372 A | 6/1986 | Beranek | |
| 4,777,955 A | 10/1988 | Brayton et al. | |
| 5,237,996 A | 8/1993 | Waldman et al. | |
| RE34,502 E | 1/1994 | Webster, Jr. | |
| 5,282,845 A | 2/1994 | Bush et al. | |
| 5,313,943 A * | 5/1994 | Houser et al. | 600/374 |

(Continued)

FOREIGN PATENT DOCUMENTS

| | | |
|---|---|---|
| DE | 19915689 A1 | 10/1999 |
| EP | 1 120 082 A1 | 8/2001 |

(Continued)

OTHER PUBLICATIONS

Extended EP Search Report dated Jul. 3, 2013 in European application No. 13160122.1 (7 pages).

(Continued)

*Primary Examiner* — Lee S Cohen
(74) *Attorney, Agent, or Firm* — Lewis Roca Rothgerber Christie LLP

(57) ABSTRACT

An improved catheter particularly useful for tubular regions at or near the heart has a distal assembly having at least two spines, each having a proximal end fixed to the catheter and a free distal end. Each spine has a support arm supporting the spine in a generally L-shaped configuration when the spine is in a relaxed, neutral state and in a generally U-shaped configuration when the spine is inserted into a tubular region. The spine has a proximal portion and a distal portion that may be straight or curved or zig-zagged. Each spine carries a tip electrode and at least one ring electrode that come into contact simultaneously with heart tissue for ablation and/or sensing electrical activity along two different circumferences of the tubular region simultaneously.

21 Claims, 14 Drawing Sheets

(56) References Cited

U.S. PATENT DOCUMENTS

| | | | | |
|---|---|---|---|---|
| 5,327,889 | A | 7/1994 | Imran | |
| 5,391,199 | A | 2/1995 | Ben-Haim | |
| 5,411,025 | A | 5/1995 | Webster, Jr. | |
| 5,433,198 | A | 7/1995 | Desai | |
| 5,443,489 | A | 8/1995 | Ben-Haim | |
| 5,480,422 | A | 1/1996 | Ben-Haim | |
| 5,546,951 | A | 8/1996 | Ben-Haim | |
| 5,551,426 | A | 9/1996 | Hummel et al. | |
| 5,555,883 | A | 9/1996 | Avitall | |
| 5,558,091 | A | 9/1996 | Acker et al. | |
| 5,567,901 | A | 10/1996 | Gibson et al. | |
| 5,568,809 | A | 10/1996 | Ben-haim | |
| 5,607,462 | A | 3/1997 | Imran | |
| 5,628,313 | A | 5/1997 | Webster, Jr. | |
| 5,683,384 | A | 11/1997 | Gough et al. | |
| 5,702,438 | A | 12/1997 | Avitall | |
| 5,722,401 | A | 3/1998 | Pietroski et al. | |
| 5,722,402 | A | 3/1998 | Swanson et al. | |
| 5,728,143 | A | 3/1998 | Gough et al. | |
| 5,730,704 | A | 3/1998 | Avitall | |
| 5,741,214 | A | 4/1998 | Ouchi et al. | |
| 5,772,590 | A | 6/1998 | Webster, Jr. | |
| 5,782,239 | A | 7/1998 | Webster, Jr. | |
| 5,855,552 | A | 1/1999 | Houser et al. | |
| 5,855,576 | A | 1/1999 | LeVeen et al. | |
| 5,897,529 | A | 4/1999 | Ponzi | |
| 5,897,554 | A | 4/1999 | Chia et al. | |
| 5,908,446 | A | 6/1999 | Imran | |
| 5,928,228 | A | 7/1999 | Kordis et al. | |
| 5,935,102 | A | 8/1999 | Bowden et al. | |
| 5,938,694 | A | 8/1999 | Jaraczewski et al. | |
| 5,951,547 | A | 9/1999 | Gough et al. | |
| 6,024,739 | A | 2/2000 | Ponzi et al. | |
| 6,064,905 | A | 5/2000 | Webster, Jr. et al. | |
| 6,068,629 | A | 5/2000 | Haissaguerre et al. | |
| 6,071,280 | A | 6/2000 | Edwards et al. | |
| 6,120,476 | A | 9/2000 | Fung et al. | |
| 6,123,699 | A | 9/2000 | Webster, Jr. | |
| 6,144,870 | A | 11/2000 | Griffin, III | |
| 6,163,716 | A | 12/2000 | Edwards et al. | |
| 6,171,277 | B1 | 1/2001 | Ponzi | |
| 6,183,463 | B1 | 2/2001 | Webster, Jr. | |
| 6,206,874 | B1 | 3/2001 | Ubby et al. | |
| 6,216,044 | B1 | 4/2001 | Kordis | |
| 6,221,107 | B1 | 4/2001 | Steiner et al. | |
| 6,231,570 | B1 | 5/2001 | Tu et al. | |
| 6,237,605 | B1 | 5/2001 | Vaska et al. | |
| 6,254,599 | B1 | 7/2001 | Lesh et al. | |
| 6,266,552 | B1 | 7/2001 | Slettenmark | |
| 6,285,898 | B1 | 9/2001 | Ben-Haim | |
| 6,292,695 | B1 | 9/2001 | Webster, Jr. et al. | |
| 6,330,473 | B1 | 12/2001 | Swanson et al. | |
| 6,332,880 | B1 | 12/2001 | Yang et al. | |
| 6,374,476 | B1 | 4/2002 | Ponzi et al. | |
| 6,389,311 | B1 | 5/2002 | Whayne et al. | |
| 6,402,740 | B1 | 6/2002 | Ellis et al. | |
| 6,402,746 | B1 | 6/2002 | Whayne et al. | |
| 6,542,781 | B1 | 4/2003 | Koblish et al. | |
| 6,574,492 | B1 | 6/2003 | Ben-Haim et al. | |
| 6,600,948 | B2 | 7/2003 | Ben-Haim et al. | |
| 6,905,495 | B1 | 6/2005 | Fuimaono et al. | |
| 6,932,814 | B2 | 8/2005 | Wood | |
| 6,961,602 | B2 * | 11/2005 | Fuimaono et al. | 600/374 |
| 6,992,477 | B2 | 1/2006 | Govari | |
| 7,025,768 | B2 | 4/2006 | Elliott | |
| 7,160,296 | B2 | 1/2007 | Pearson et al. | |
| 7,366,557 | B2 * | 4/2008 | Bautista | 600/372 |
| 7,387,628 | B1 | 6/2008 | Behl et al. | |
| 7,416,549 | B2 | 8/2008 | Young et al. | |
| 7,496,394 | B2 * | 2/2009 | Ahmed et al. | 600/381 |
| 7,722,606 | B2 | 5/2010 | Azure | |
| 7,806,893 | B2 | 10/2010 | Ostrovsky et al. | |
| 7,818,048 | B2 * | 10/2010 | Plaza | 600/509 |
| 8,439,909 | B2 * | 5/2013 | Wang et al. | 606/41 |
| 2001/0001819 | A1 | 5/2001 | Lee et al. | |
| 2002/0026188 | A1 | 2/2002 | Balbierz et al. | |
| 2002/0068867 | A1 | 6/2002 | Ameling et al. | |
| 2002/0072742 | A1 | 6/2002 | Schaefer et al. | |
| 2002/0087157 | A1 | 7/2002 | Sliwa, Jr. et al. | |
| 2002/0133150 | A1 | 9/2002 | Whayne et al. | |
| 2002/0183638 | A1 | 12/2002 | Swanson | |
| 2003/0050637 | A1 | 3/2003 | Maguire et al. | |
| 2003/0125614 | A1 | 7/2003 | Fuimaono et al. | |
| 2003/0171746 | A1 | 9/2003 | Fleischman | |
| 2004/0044277 | A1 | 3/2004 | Fuimaono et al. | |
| 2004/0153056 | A1 | 8/2004 | Muller et al. | |
| 2005/0240174 | A1 | 10/2005 | Pearson et al. | |
| 2006/0089634 | A1 | 4/2006 | Anderson et al. | |
| 2009/0209950 | A1 | 8/2009 | Starksen | |
| 2010/0010487 | A1 | 1/2010 | Phan et al. | |
| 2010/0076426 | A1 | 3/2010 | de la Rama et al. | |
| 2011/0257649 | A1 * | 10/2011 | Geistert et al. | 606/41 |
| 2012/0172703 | A1 | 7/2012 | Esguerra et al. | |
| 2013/0030426 | A1 * | 1/2013 | Gallardo et al. | 606/33 |
| 2013/0253503 | A1 * | 9/2013 | Govari et al. | 606/41 |

FOREIGN PATENT DOCUMENTS

| | | | |
|---|---|---|---|
| EP | 1 266 613 A1 | 12/2002 | |
| EP | 1 323 375 A2 | 7/2003 | |
| EP | 1 417 936 A1 | 5/2004 | |
| EP | 1 992 300 A2 | 11/2008 | |
| WO | WO 95/02995 | 2/1995 | |
| WO | WO 96/05768 | 2/1996 | |
| WO | WO 97/24981 | 7/1997 | |
| WO | WO 97/24983 | 7/1997 | |
| WO | WO 98/29033 | 7/1998 | |
| WO | WO 99/52423 A1 | 10/1999 | |

OTHER PUBLICATIONS

European Search Report dated Aug. 21, 2003 from European Patent Application No. EP02259006.1.

European Search Report dated Mar. 18, 2004 from European Patent Application No. EP03256844.6.

* cited by examiner

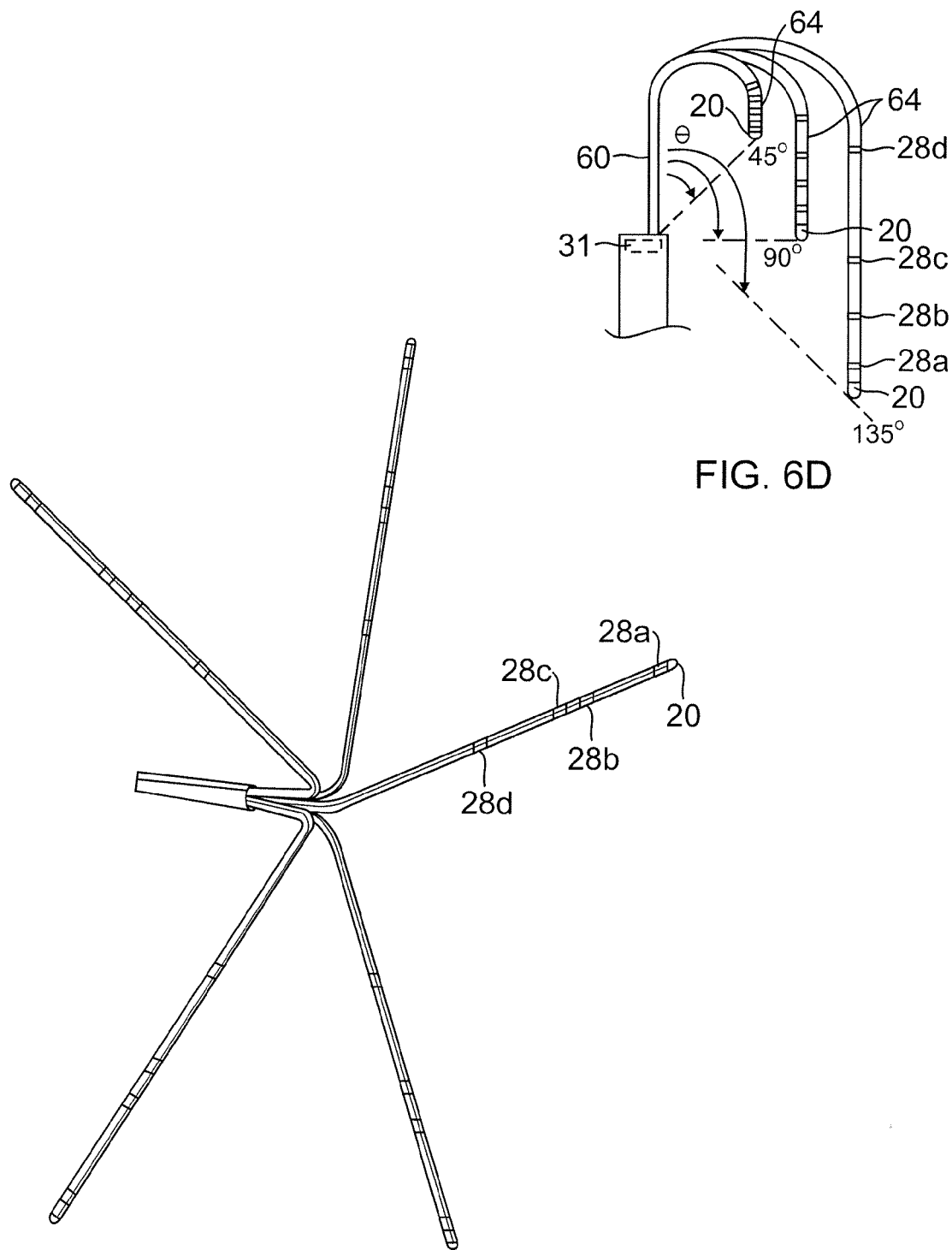

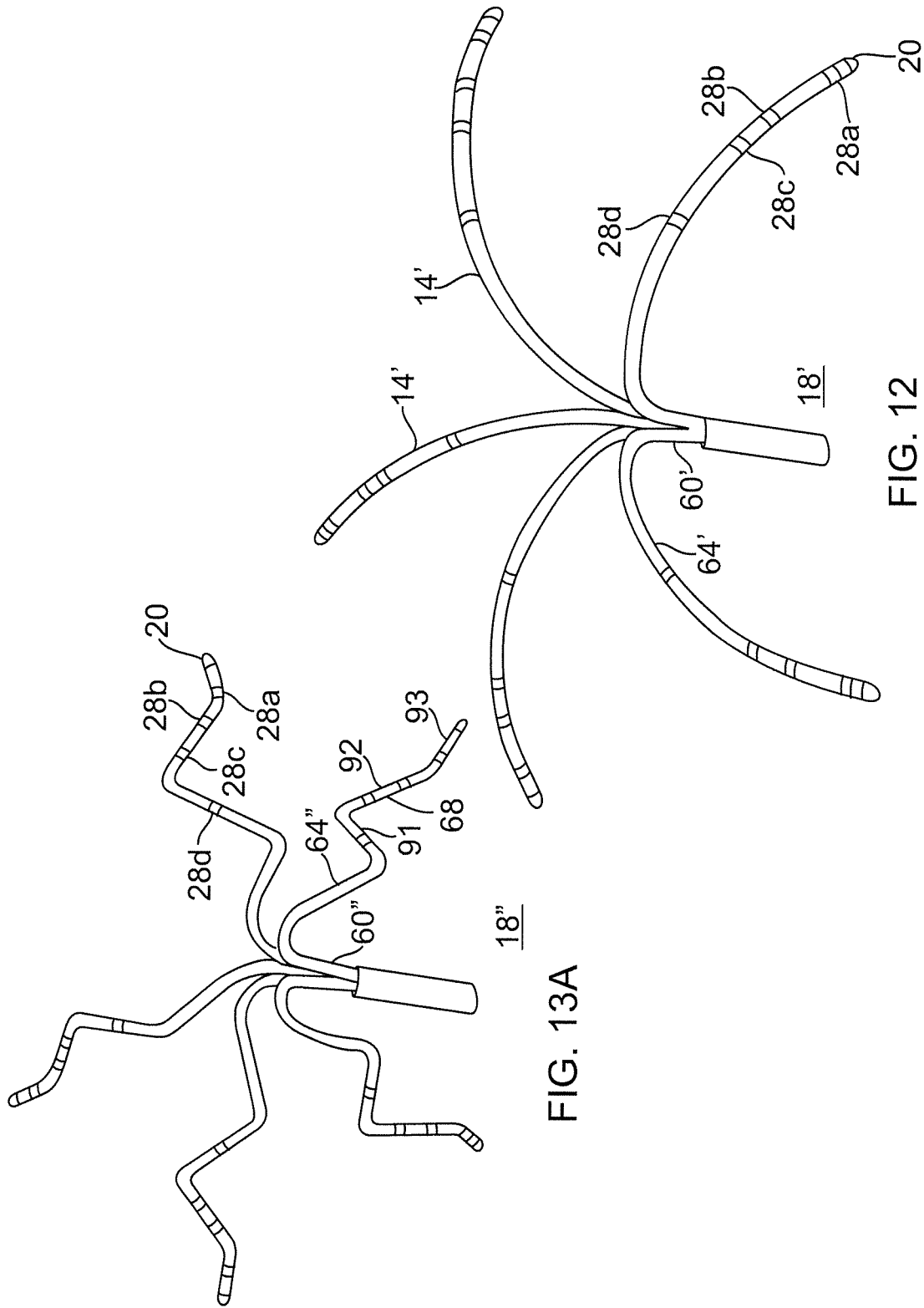

FLOWER CATHETER FOR MAPPING AND ABLATING VEINOUS AND OTHER TUBULAR LOCATIONS

BACKGROUND OF THE INVENTION

Electrode catheters have been in common use in medical practice for many years. They are used to stimulate and map electrical activity in the heart and to ablate sites of aberrant electrical activity. In use, the electrode catheter is inserted into a chamber of the heart. Once the catheter is positioned, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with or in close proximity to the endocardium. By monitoring the electrical signals at the endocardium, aberrant conductive tissue sites responsible for the arrhythmia can be pinpointed.

For mapping, it is desirable to have a relatively small mapping electrode. It has been found that smaller electrodes record more accurate and discrete electrograms. Additionally, if a bipolar mapping arrangement is used, it is desirable that the two electrodes of the mapping arrangement be in close proximity to each other and that they be similar in size to produce more accurate and useful electrograms.

Once the origination point for the arrhythmia has been located in the tissue, the physician uses an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

A typical ablation procedure involves providing a reference electrode, generally taped to the skin of the patient. RF (radio frequency) current is applied to the tip electrode, and current flows through the media that surrounds it, i.e., blood and tissue, toward the reference electrode. Alternatively, the catheter may carry bipolar electrodes, in which instance, the current flows from the tip electrode, through the media and toward another electrode carried on the catheter tip. In any case, the distribution of current depends on the amount of electrode surface in contact with the tissue as compared to blood, which has a higher conductivity than the tissue. Heating of the tissue occurs due to electrical current. The tissue is heated sufficiently to cause cellular destruction in the cardiac tissue resulting in formation of a lesion within the cardiac tissue which is electrically non-conductive.

A disadvantage with current catheters is where the aberrant activity originates in a vein or other tubular structure leading away from the heart chamber. In the case of electrophysiological triggers in such locations, a common alternative to the ablation of the tissue that generates the triggers involves ablating a lesion to interrupt wavelets, for example, when ablating a line of block. For tubular regions in or around the heart, this procedure requires the line of block to be made about a circumference of the tubular region. However, it is difficult to manipulate and control the distal end of a straight catheter so that it effectively ablates about the circumference. Moreover, although most vessels have circular cross-sections, many do not and they come in different sizes. Accordingly, a need exists for an improved catheter that is particularly useful for such applications Flower mapping catheters are known; however, conventional flower catheters carry smaller electrodes which are not well suited for ablation. Furthermore, existing flower catheters were developed for atrial diagnostics, not vein mapping or ablation which pose different challenges.

Lasso catheters are also known. However, lasso catheters have a generally circular main portion which is not always adaptable to noncircular tubular structures. Moreover, the generally circular main portion is typically positioned along a single circumference of the tubular structure for forming a line of isolation. As such, testing the line of isolation for completion requires repositioning the catheter, ire-use of a second catheter, both of which increase the duration, complexity and/or cost of the ablation procedure.

Thus, there is a desire for a catheter adapted for mapping and ablation in a tubular structure, especially a tubular structure with a noncircular cross-section. It is further desired that the catheter be adapted for testing completeness of ablation isolation lines without the need for repositioning or the use of an additional catheter.

SUMMARY OF THE INVENTION

The present invention is directed to an improved catheter for ablating tubular regions at or near the heart. The catheter comprises a distal assembly having a plurality of spines, each capable of ablating and/or obtaining electrical data from the heart tissue. The use of a plurality of spines extending radially outward from the catheter ensures contact between the spines and surrounding tissue generally without regard to the size or shape of the tubular region. Because each spine is fixed only at its proximal end, the free distal end of each spine can independently adapt to the tubular region, especially if the tubular region has a noncircular cross-section. Each spine has a generally L-shaped configuration with a generally straight proximal portion, and a distal portion that is generally orthogonal to the proximal portion. Advantageously, the generally L-shaped configuration converts into a generally U-shaped configuration with the distal portion lying against the surrounding tissue for greater contact once the proximal portion is pushed or advanced into the tubular cavity. It is understood that the change in configuration is enabled and occurs where the radial size of the tubular cavity is sufficiently small relative to the length or "reach" of the distal portion such that the distal end of the distal portion can contact with the surrounding tissue of the tubular cavity. Such greater contact along the distal portion enables a tip electrode and at least one ring electrode, both carried on the distal portion of each spine, to make simultaneous contact with the surrounding heart tissue along two different inner circumferences of the tubular region, where a first inner circumference is defined by contact with the tip electrode of each spine and at least a second inner circumference advantageously deeper in the tubular region is defined by contact with at least one ring electrode of each spine.

In one embodiment, the catheter comprising an elongated catheter body having a proximal end, a distal end and at least one lumen extending longitudinally therethrough. The distal assembly comprises about five spines. Each spine includes a nonconductive covering and a support arm with shape memory extending therein. The distal assembly includes a spine mounting assembly that fixes proximal ends of each spine to the distal end of the catheter body. Each spine has a generally L-shaped configuration with a generally straight proximal portion, and a distal portion that is generally orthogonal to the proximal portion and carries a tip electrode and at least one ring electrode. Depending on various parameters, including length and/or curvature of each portion of the spine, the distal end or tip electrode of the spine when adopting a generally U-shaped configuration within a tubular cavity defines an angle θ with the proximal end of the spine. The angle θ ranges between about 45 and 135 degrees, preferably between about 65 and 115 degrees, and preferably about 90 degrees. Where the angle θ is less than 90 degrees, the distal end is distal of the proximal end of the spine. Where the angle θ is about 90 degrees, the distal end is about even with the proximal end of the spine 14. Where the angle θ is greater than 90 degrees, the distal end is proximal of the proximal end of the spine. However, regardless of the angle θ, the generally U-shaped configuration of the spine when the proximal portion is advanced into the tubular cavity ensures that the ring electrodes are predictably and consistently positioned deeper in the tubular region than the tip electrodes. In alternate embodiments, each spine may have a nonlinear distal portion with a curved configuration or a zig-zag configuration.

The catheter of the present invention may include a steering mechanism for uni- or bi-directional deflection. In one embodiment, an intermediate deflectable section extends between the catheter body and the distal assembly and deflection is actuated by one puller wire or a pair of puller wires that extend from a control handle to a distal end of the intermediate deflectable section. A compression coil surrounds each puller wire in the catheter body. Mechanism for actuating the puller wire(s) are provided in the control handle for manipulation by the user.

The present invention is also directed to a method of ablating a tubular region at or near the heart. A method for ablating a tubular structure of the heart includes introducing the distal assembly of the above catheter having L-shaped spines into the tubular region and positioning the distal assembly so that the one tip electrode from each spine is in contact with heart tissue. The method includes advancing the distal assembly deeper into the tubular region such that the L-shaped spines changes to a U-shape where the tip electrode of each spine is in contact with heart tissue along a first inner circumference of the tubular structure and at least one ring electrode from each spine is in contact with heart tissue along a second inner circumference of the tubular structure deeper into the tubular region than the first inner circumference. The method includes energizing at least one electrode (tip or ring) on each spine to ablate along the respective circumference. The method includes sensing electrical activity of the tubular region by the other electrodes of each spine during, after or between the ablation to assess the lesions formed by the ablating electrodes. Advantageously, the sensing of electrical activity can occur without repositioning of the distal assembly and while the electrodes performing the ablation are in contact with the heart tissue.

DESCRIPTION OF THE DRAWINGS

These and other features and advantages of the present invention will be better understood by reference to the following detailed description when considered in conjunction with the accompanying drawings wherein:

FIG. 1A is an enlarged view of a distal assembly of FIG. 1.

FIG. 6D is a schematic drawing of various embodiments of a spine in a U-shaped configuration in accordance with the invention.

FIG. 12 is a perspective view of a distal assembly (with spines in a neutral state) in accordance with another embodiment of the invention.

FIG. 13A is a perspective view of a distal assembly (with spines in a neutral state) in accordance with yet another embodiment of the invention.

DETAILED DESCRIPTION OF THE INVENTION

Figure 1:
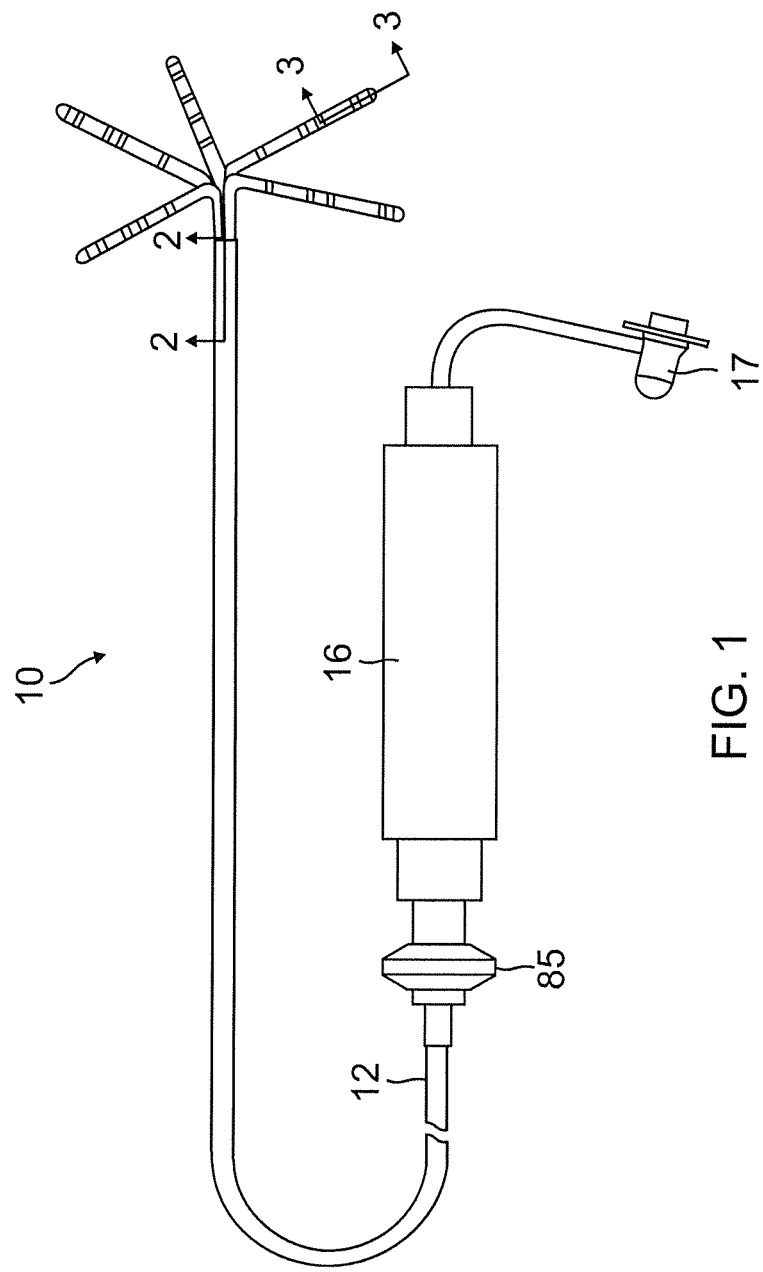
FIG. 1 is a perspective view of a catheter according to an embodiment of the invention.

The invention is directed to a catheter 10 as shown in FIG. 1, having a distal assembly 18 comprising a plurality of spines 14. Each spine carries at least one electrode, preferably a tip electrode 20 and at least one ring electrode 28, such that when the spines are positioned in contact with tissue of a tubular structure at or near the heart, each spine is capable of obtaining electrical data and ablating tissue. As shown in FIG. 1, the catheter 10 comprises an elongated catheter body 12 having proximal and distal ends, a control handle 16 at the proximal end of the catheter body 12, and a distal assembly 18 comprising a plurality of spines 14 mounted at the distal end of the catheter body 12.

Figure 2:
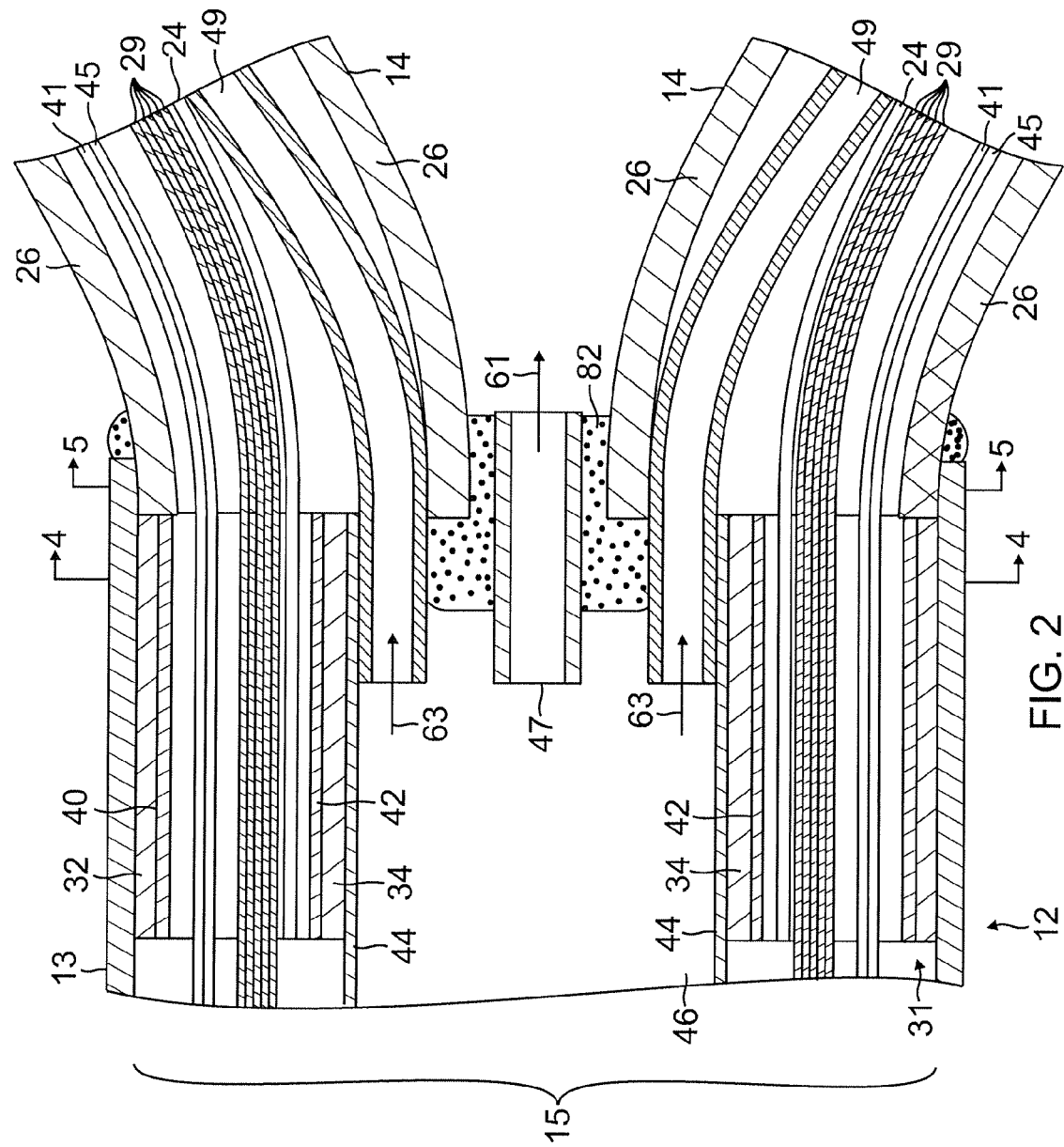
FIG. 2 is a side cross-sectional view of a portion of the catheter of FIG. 1, including a junction between a catheter body and a spine, taken along line 2-2.

As shown in FIGS. 1 and 2, the catheter body 12 comprises an elongated tubular construction having a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 13 made of polyurethane or PEBAX® (polyether block amide). The outer wall 13 comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 13 is not critical, but is preferably thin enough so that the central lumen 15 can accommodate lead wires, sensor cables and any other wires, cables or tubes. If desired, the inner surface of the outer wall 13 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In the depicted embodiment, the distal assembly 18 comprises five spines 14. Each spine 14 has a proximal end attached at the distal end of the catheter body 12 and a free distal end, i.e., the distal end is not attached to any of the other spines, to the catheter body, or to any other structure that confines movement of the distal end. Each spine 14 contains a support arm 24 comprising a metal or plastic material that has shape memory, such that the support arm 24 forms an initial shape when no external forces, are applied, forms a deflected shape when an external force is applied, and returns to its initial shape when the external force is released. In a preferred embodiment, the support arm 24 comprises a superelastic material, for example a nickel-titanium alloy, such as nitinol. Each spine 14 also comprises a non-conductive covering 26 in surrounding relation to the support arm 24. In a preferred embodiment, the non-conductive covering 26 comprises a biocompatible plastic tubing, such as a polyurethane or polyimide tubing.

As will be recognized by one skilled in the art, the number of spines 14 can vary as desired depending on the particular application, so that the catheter 10 has at least two spines, preferably at least three spines, more preferably at least five spines and as many as eight, ten or more spines. For clarity however only two spines are shown in FIG. 2. As described in more detail below, the spines 14 are moveable between an expanded arrangement, wherein, for example, each spine extends radially outwardly from the catheter body 12 in a generally L-shaped configuration, or the spines 14 may be arranged in a collapsed arrangement, wherein, for example, each spine is disposed generally along a longitudinal axis of the catheter body 12 so that the spines are capable of fitting within a lumen of a guiding sheath, as discussed further below.

Figure 3:
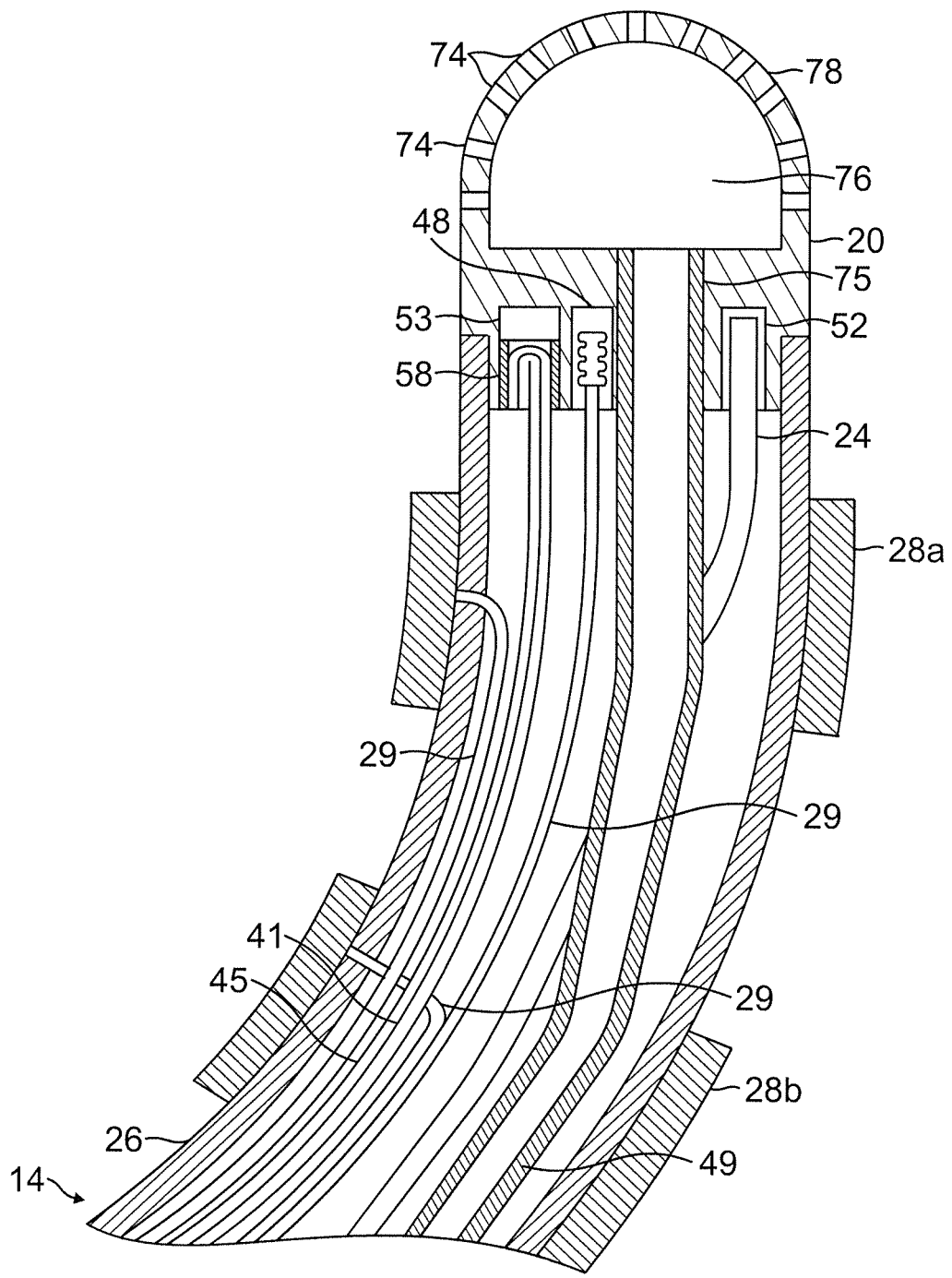
FIG. 3 is a side cross-sectional view of a spine of the catheter of FIG. 1, taken along line 3-3.

With reference to FIG. 3, each spine 14 carries at least one electrode mounted along its length at or near its distal end. In the depicted embodiment, a tip electrode 20 is mounted on a distal end of each non-conductive covering 26 and at least a first ring electrode 28a is mounted on each non-conductive covering 26 on the distal end of the non-conductive covering 26. The distance between the tip electrode 20 and ring electrode 28a preferably ranges from about 0.5 mm to about 2.0 mm. Additional single or pair of ring electrodes 28b-28d may be mounted on each non-conductive covering 26 proximal of the first ring electrode 28a. In the depicted embodiment, the catheter is configured so that the tip electrode functions with a distal-most ring electrode as a distal electrode pair. An alternate embodiment of the catheter may be utilize the tip electrode for unipolar electrograms only, where the distance between the tip electrode and the distal-most ring electrode 28a would be greater. In the depicted embodiment, the distance between the first ring electrode 28a and adjacent electrode 28b ranges from about 0.5 mm to about 2.0 mm. The distance between adjacent pairs of electrode ranges from about 2.0 mm to about 8.0 mm. The distance between ring electrodes of one pair ranges from about 0.5 mm to about 2.0 mm. Any of the ring electrodes 28a-28d may be used for either unipolar or bipolar electrogram measurement. That is, the tip and ring electrodes may be used in conjunction with one or more reference electrodes attached to outside the body of the patient (e.g., in the form of a patch), or any of the ring electrodes may function as a reference electrode.

Each tip electrode 20 has an exposed length preferably ranging from about 0.5 mm to about 4.0 mm, more preferably from about 0.5 mm to about 2.0 mm, still more preferably about 1.0 mm. Each ring electrode 28 has a length preferably up to about 2.0 mm, more preferably from about 0.5 mm to about 1.0 mm.

Each tip electrode 20 and each ring electrode 28 is electrically connected to an electrode lead wire 29, which in turn is electrically connected to a connector 17 (FIG. 1). The connector 17 is connected to an appropriate mapping or monitoring system (not shown). Each electrode lead wire 29 extends from the connector 17, through the control handle 16, through the central lumen 15 in the catheter body 12, and into the non-conductive covering 26 of the spine 14 where it is attached to its corresponding tip electrode 20 or ring electrode 28. Each lead wire 29, which includes a non-conductive coating (not shown) over almost all of its length, is attached to its corresponding tip electrode 20 or ring electrode 28 by any suitable method to ensure electrical conduction.

One method for attaching a lead wire 29 to a ring electrode 28 involves first making a small hole through an outer wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 may be formed by wrapping the lead wire 29 around the non-conductive covering 26 a number of times and stripping the lead wire of its own non-conductive coating on its outwardly facing surfaces. In such an instance, the lead wire 29 functions as a ring electrode.

Each spine 14 can also include at least one temperature sensor, e.g., a thermocouple or thermistor, for the tip electrode 20 or any of the ring electrodes. In the depicted embodiment, a thermocouple is formed by an enameled wire pair. One wire of the wire pair is a copper wire 41, e.g., a number "40" copper wire. The other wire of the wire pair is a constantan wire 45. The wires 41 and 45 of the wire pair are electrically isolated from each other except at their distal ends where they are twisted together, covered with a short thin piece of plastic tubing 58, e.g., polyamide, and covered with epoxy with good thermal conductive coefficient.

The wires 41 and 45 extend through the central lumen 15 of the catheter body 12 (FIG. 2). Within the central lumen 15, the wires 41 and 45 extend through a protective sheath (not shown) along with the lead wires 29. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143E/37C sold by Thermometrics (New Jersey).

FIG. 3 illustrates a suitable technique for mounting the tip electrode lead wire 29, the thermocouple wires 41 and 45 and the support arm 24 to the tip electrode 20. A distal end of the electrode lead wire 29 may be secured to the tip electrode 20 by drilling a first blind hole 48 into the tip electrode 20, stripping the lead wire 29 of any coating and placing the lead wire 29 within the first blind hole 48 where it is electrically connected to the tip electrode 20 by a suitable means, such as by soldering or welding. The lead wire 29 may then be fixed in place, for example, by using a polyurethane glue or the like. The support arm 24 may also be similarly affixed to the tip electrode 20. For example, a second blind hole 52 may be drilled into the tip electrode 20 such that a distal end of the support arm 24 may be inserted into the second blind hole 52 and affixed therein, for example, using a polyurethane glue or the like. Moreover, a third blind hole 53 may be drilled into the tip electrode 20 such that the plastic tubing 58 surrounding distal ends of the thermocouple wires 41 and 45 may be inserted into the third blind hole and affixed therein, using a polyurethane glue or the like. Alternatively, the wires 41 and 45 can be soldered into the blind hole 53.

Alternatively, a single blind hole (not shown) in the proximal end of the tip electrode 20 can be used for mounting the support arm 24 and thermocouple wires 41 and 45, and the distal end of the lead wire 29 can be wrapped around the outside proximal end of the tip electrode, which is not exposed and attached by solder, welding or any other suitable technique. Any other arrangement for mounting these components in the spine could also be used.

Figure 4:
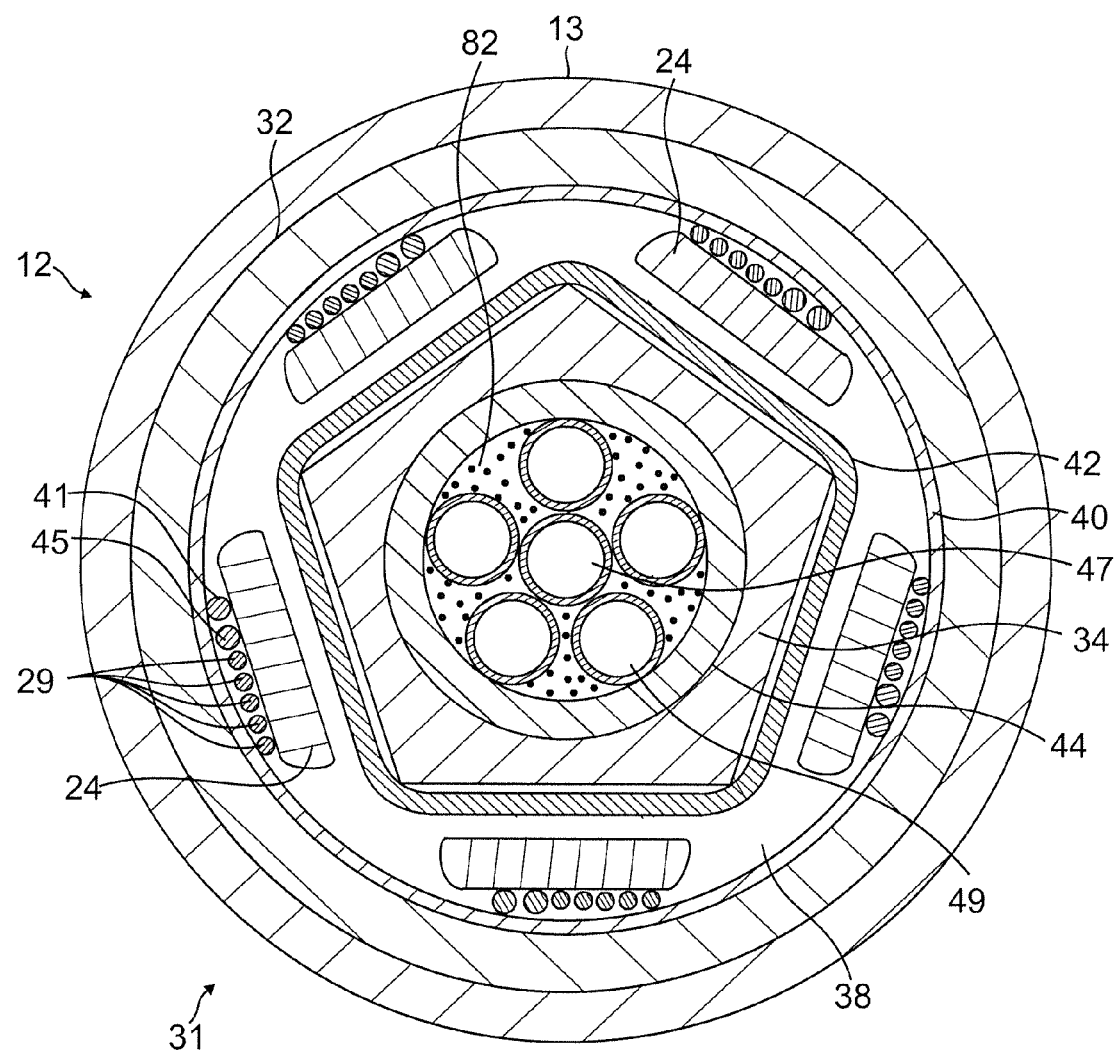
FIG. 4 is an end cross-sectional view of the junction of FIG. 2, taken along line 4-4.

A suitable construction of the distal end of the catheter body 12, having spines 14 mounted thereto, is depicted in FIGS. 2 and 4. Again, for clarity, only two spines 14 are shown in FIG. 2. Mounted in the distal end of the lumen 15 of the catheter body 12 is a spine mounting assembly 31 that secures the proximal ends of the spines to the catheter. In the illustrated embodiment, the spine mounting assembly 31 comprises an outer mounting ring 32 disposed within the outer wall 13 of the catheter body 12. The outer mounting ring 32 preferably comprises a metal material, such as stainless steel, more particularly stainless steel 303, and may be attached at the distal end of the catheter body 12 by a variety of methods, such as by welding or by use of an adhesive, such as a polyurethane glue. Alternatively, the outer mounting ring 32 may comprise a plastic material. A mounting structure 34 is provided coaxially within the outer mounting ring 32. In the depicted embodiment, the mounting structure 34 is multi-sided and comprises a metal material, such as stainless steel, more particularly stainless steel 303. The mounting structure 34 may also alternatively comprise a plastic material. The outer mounting ring 32 and the mounting structure 34 provide a channel 38 therebetween in which the proximal end of each support arm 24 is mounted. Specifically, each spine 14 is mounted in the catheter body 12 by removing a portion of the non-conductive covering 26 at the proximal end of each spine 14, inserting the exposed proximal end of each support arm 24 into the channel 38 between the outer mounting ring 32 and the multi-sided mounting structure 34 and affixing within the channel 38 by any suitable means, such as with a polyurethane glue or the like. The lead wires 29 and thermocouple wires 41 and 45 also extend through the channel 38 between the outer mounting ring 32 and the mounting structure 34.

Figure 5:
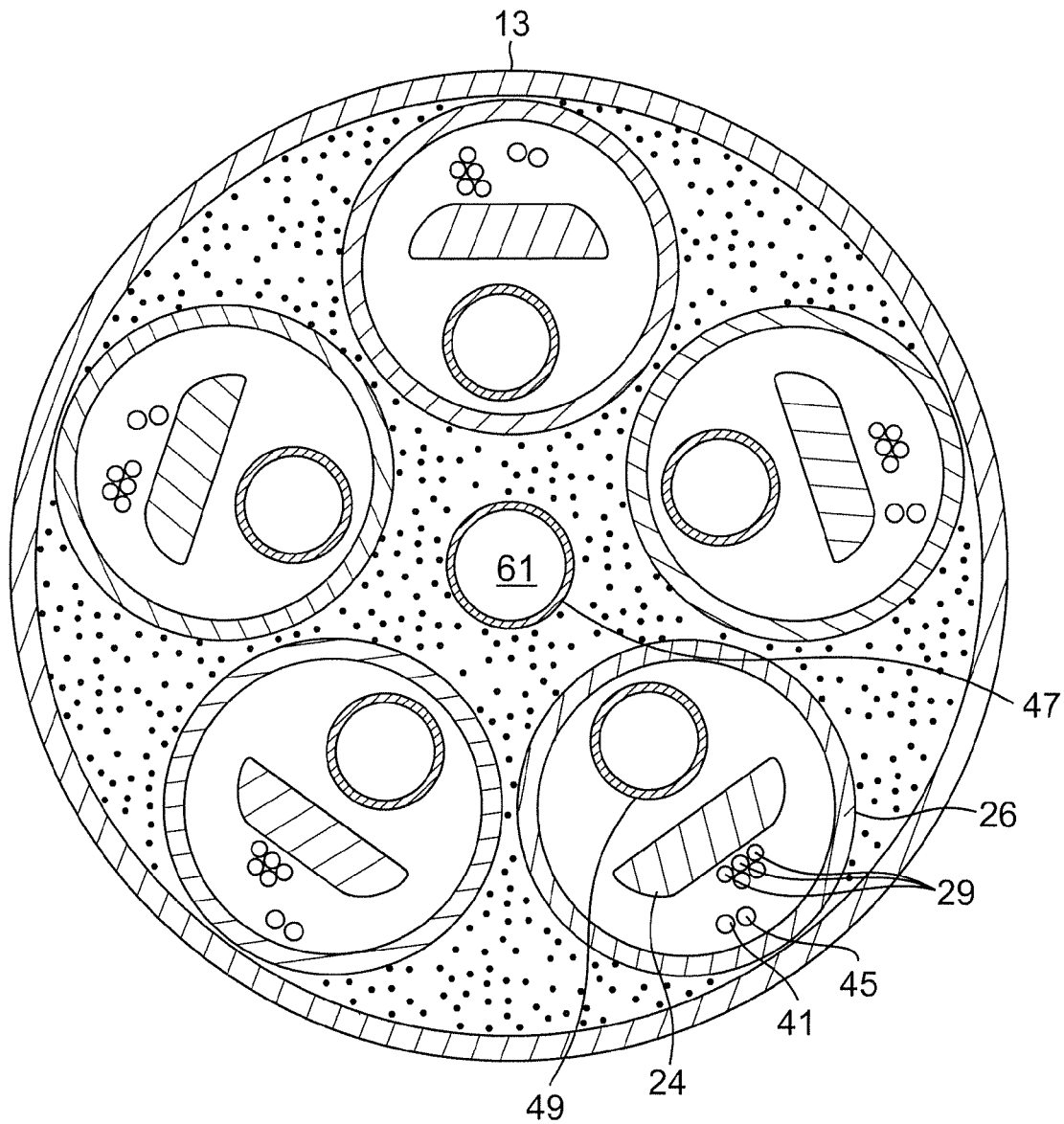
FIG. 5 is an end cross-sectional view of the junction of FIG. 2, taken along line 5-5.

In one embodiment, the support arm 24 has a generally trapezoidally-shaped end cross section with curved sides as illustrated in FIGS. 4 and 5. In such an arrangement, when each support arm 24 is inserted into the channel 38, a substantially flat surface of each support arm 24, preferably the base of the trapezoidally-shaped end cross section, is mounted against a substantially flat surface on the multi-sided mounting structure 34. Preferably the number of substantially flat outer surfaces on the multi-sided mounting structure 34 corresponds to the number of spines 14. In such an instance, the support arm 24 of each spine 14 may be mounted within the channel 38 and adjacent to its corresponding side on the multi-sided mounting structure 34 to enable the support arms 24, and thus the spines 14, to be equally spaced around the multi-sided mounting structure 34. The multi-sided mounting structure 34 may be approximately co-axial with the longitudinal axis of the catheter body 12 such that the spines 14 are equally spaced about the catheter body 12 as well. Once each support arm 24 is properly positioned within the channel 38, each support arm 24 may be affixed within the channel 38 by any suitable means, such as by use of an adhesive, such as a polyurethane glue. Alternatively, the mounting structure 34 can have a round outer surface, although with such an embodiment more care needs to be taken if the support arms 24 are to be evenly spaced about the mounting structure.

In the depicted embodiment, a first non-conducting tube 40 is disposed between the outer mounting ring 32 and the support arms 24, and a second non-conducting tube 42 is disposed between the support arms 24 and the mounting structure 34. The non-conducting tubes 40 and 42, which may be polyimide tubes, ensure that each support arm 24 remains electrically isolated.

Figure 6A:
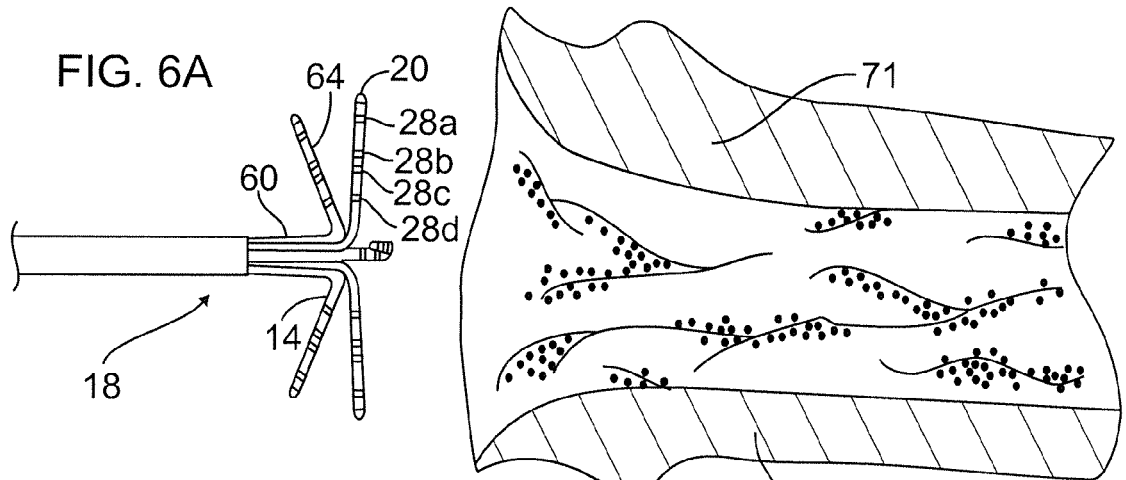
FIG. 6A is a side view of a distal assembly advancing toward a tubular region according to an embodiment of the invention, with spines of the distal assembly in a generally relaxed L-shaped configuration.
Figure 6B:
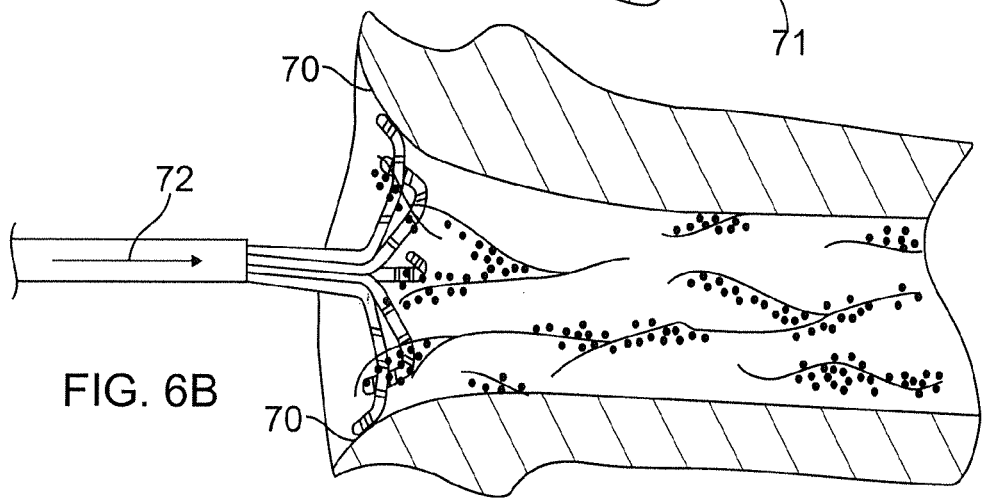
FIG. 6B is a side view of the distal assembly of FIG. 6A entering a tubular region, with spines of the distal assembly.
Figure 6C:
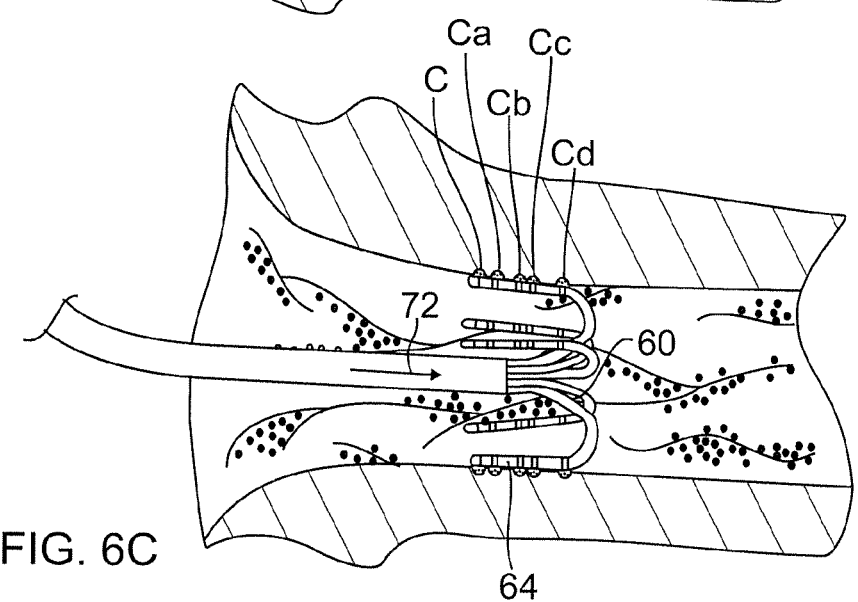
FIG. 6C is a side view of the distal assembly of FIG. 6A positioned in a tubular region, with spines of the distal assembly in a generally U-shaped configuration.

In accordance with a feature of the invention, each spine 14 has a generally L-shaped configuration supported by the support arm 24. In the illustrated embodiment of FIGS. 1 and 6, the generally L-shaped configuration of each spine is defined by a generally straight proximal portion 60, a generally straight distal portion 64 that extends at a generally orthogonal angle from the proximal portion 60. When the distal assembly 18 is initially deployed in a tubular cavity 71, as illustrated in FIG. 6A, the spines 14 are in their generally neutral and relaxed L-shaped configuration. As the distal assembly enters the tubular cavity as illustrated in FIG. 6B, the distal ends of the spines come into contact with an opening or ostium 70 of the tubular cavity, where the L-shaped configuration of the spines 14 starts to change under a contact force applied to the distal ends of the spines by the ostium. When the distal assembly 18 is advanced, the proximal portions 60 of the spines are pushed deeper into the tubular cavity and the distal ends of the spines 14 come into contact with tissue lining the tubular cavity 71. The distal assembly 18 is further advanced so that the distal portions 64 increasingly bend over the distal ends until more of the distal portions 64 also come into contact with deeper tissue in the tubular cavity 71 whereupon the spines 14 are in a generally U-shaped configuration as shown in FIG. 6C. Depending on various parameters, the distal end or tip electrode 20 of the spine in the generally U-shaped configuration defines an angle $\theta$ with the proximal end of the spine. The angle $\theta$ ranges between about 45 and 135 degrees, preferably between about 80 and 100 degrees, and preferably about 90 degrees, as illustrated in FIG. 6D. Where the angle $\theta$ is less than 90 degrees, the tip electrode 20 is distal of the proximal end of the spine 14 at the spine mounting assembly 31. Where the angle $\theta$ is about 90 degrees, the tip electrode 20 is about even with the proximal end of the spine 14. Where the angle θ is greater than 90 degrees, the tip electrode 20 is proximal of the proximal end of the spine 14. However, regardless of the angle θ, the generally U-shaped configuration of the support member 24 (and hence the spine 14) provides that the distal portion 64 is nearly parallel with the generally straight proximal portion 60 and that the ring electrodes 28 are consistently positioned deeper in the tubular structure than the tip electrode 20. As illustrated in FIG. 6D, the length and/or curvature of each portion 60 and 64 can be varied as desired or appropriate. Moreover, the length, curvature and/or angle θ need not be uniform for each spine throughout the distal assembly. For example, a first set of spines may have one length, curvature and/or angle θ and a second set of spines may have another length, curvature and/or angle θ. Although the spines are equally radially spaced from each other in the illustrated embodiments, the radial spacing can also be varied as desired or appropriate. In the illustrated embodiment of FIG. 6C, the catheter is illustrated as it appears when pushed into a tubular cavity. The change in configuration of the spine from a relaxed state (L-shaped) in FIG. 6A to a confined state (U-shaped) in FIB. 6C reflects how the angle θ grows when the distal assembly 18 is pushed into the tubular cavity. The length of the spine 14 extending between the exposed proximal end of the covering 26 to the distal tip end of the spine can range between about 1.0 cm and 5.0 cm.

In accordance with a feature of the present invention, when the distal assembly 18 is inserted into and confined within a tubular structure the tip electrodes 20 of the distal assembly 18 are well adapted to make contact with the surrounding tissue of a tubular structure 71 at locations spanning generally along an inner circumference C of the tubular structure. Similarly, the first ring electrodes 28a on the spines 14 are well adapted to contact tissue at locations spanning generally along another or a first adjacent inner circumference $C_a$ deeper in the tubular structure. Likewise, additional ring electrodes 28b-28d are well adapted to contact tissue at locations spanning generally along other or additional adjacent inner circumferences $C_b$-$C_d$ more deeply in the tubular structure. Rotation of the catheter by the control handle rotates the distal assembly 18 so as to rotate and shift the electrodes to different contact locations along each inner circumference. Where, for example, the tip electrodes 20 are adapted for ablation, an isolation line can be created at the circumference C and the integrity or completeness of the isolation line at the circumference C can be sensed by the ring electrodes 28a-28d at locations along adjacent circumferences $C_a$-$C_d$ further into the tubular structure. Alternatively, any of the sets of ring electrodes $28_i$ can be adapted for ablation for creating an isolation line at Ci, and any gaps in the isolation line at $C_i$ can be sensed by any of the non-ablating sets of tip or ring electrodes. Thus, ablation and testing of the resulting lesions can be advantageously accomplished by the catheter 10 without repositioning of the distal assembly 18 or use of an additional catheter.

With reference to FIGS. 2 and 4, a main irrigation tube 44 extends, e.g., coaxially, through the mounting structure 34. The irrigation tube 44 comprises a non-conductive material such as PEBAX, polyimide or polyurethane. The irrigation tube 44 extends through the catheter body 12 and out through the control handle 16 or out a sidearm (not shown) as is known in the art and described in U.S. Pat. No. 6,120,476, the disclosure of which is incorporated herein by reference. As discussed further below, the irrigation tube 44 is used to introduce irrigation fluid to the region between the spines 14 and at the tip electrodes 20 of the spines. The region between the spines is prone to thrombus formation and the ablating electrodes can overheat causing the formation of char. The distal end of the main irrigation tube 44 is preferably glued in place between the spines 14.

As illustrated in FIGS. 4 and 5, a distal end of the main irrigation tube 44 receives proximal ends of a short irrigation tube 47 for the region between the spines, and a plurality of dedicated irrigation tubes 49, one for each spine. In the illustrated embodiment, the short irrigation tube 47 positioned centrally and surrounded radially by the spine irrigation tubes 49. A lumen of the short irrigation tube 47 provides a fluid path (arrow 61) from the distal end of the main irrigation tube 44 to outside of the catheter in the region between the spines.

Each spine irrigation tube 49 arranged around the short irrigation tube 47 extends from the distal end of the main irrigation tube 44 into a respective spine 14 of the distal assembly 18. As illustrated in FIGS. 2 and 3, each spine irrigation tube 49 extends through a respective nonconductive covering 26, along with the lead wires 29, thermocouple wires 41 and 45, support arm 24 of the respective spine, where a distal end of the spine irrigation tube 44 terminates in an irrigation passage 75 that leads to a fluid chamber 76, both formed in the tip electrode 20. Irrigation apertures 74 are formed in distal wall 78 of the tip electrode 20 to allow fluid communication from the fluid chamber 76 to outside the tip electrode 20.

As illustrated in FIG. 2, irrigation fluid passing through the irrigation tube 44 travels through the control handle 16 and the catheter shaft 12. At the distal end of the irrigation tube 44, a portion of the fluid exits the catheter through the short irrigation tube 47 (arrow 61) and other portions continue into the spines (arrow 63) through the spine irrigation tubes 49. At the tip electrode 20, the irrigation fluid enters the fluid chamber 76 via the irrigation passage 75 and exits the tip electrode 20 through the irrigation apertures 74. The distal end of the main irrigation tube 44 is plugged by an adhesive or sealant 82 which also fixes the short irrigation tube 47 and proximal ends of the spine irrigation tubes 49 in the distal end of the main irrigation tube 44. As would be recognized by one skilled in the art, the main irrigation tube 44 can comprise a plurality of structures that define a continuous path through the catheter body 12 and into the handle 16, including a combination of one or more lumens and one or more tubes. The distal end of the spine irrigation tubes 49 is adhered to the spine tip electrode 20 irrigation passage 75 by an adhesive such as EPOXY or sealant.

As previously discussed, when mounting the support arms 24 to the spine mounting assembly 31, a portion of the non-conductive covering 26 at the proximal end of each spine 14 is removed to expose the support arm 24. Removing a portion of the non-conductive covering 26 at the proximal end of each spine 14 enables the electrode lead wires 29 and the thermocouple wires 41 and 45 to extend from the lumen 15 of the catheter 12, through lumen 46 of the mounting ring 32, and into each non-conductive covering 26. As shown in FIG. 2, once inserted into the non-conductive coverings 26, the electrode lead wires 29 and thermocouple wires 41 and 45 extend within the non-conductive covering 26, where the lead wires 29 are electrically connected at their distal ends to their corresponding tip electrode 20 and ring electrode 28.

Figure 7:
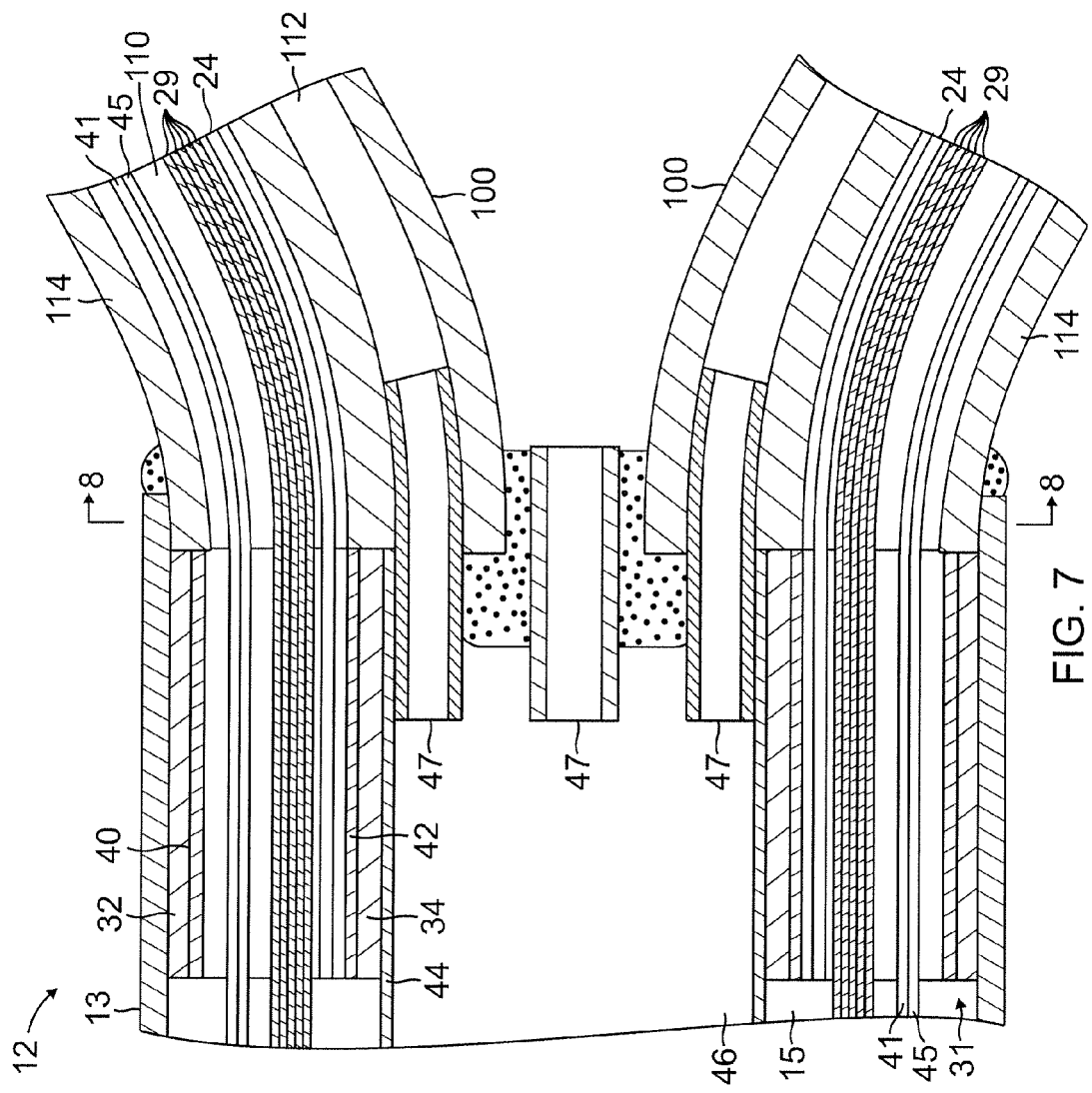
FIG. 7 is a side cross-sectional view of a portion of a catheter in accordance with another embodiment of the present invention, including a junction between a catheter body and a spine.
Figure 8:
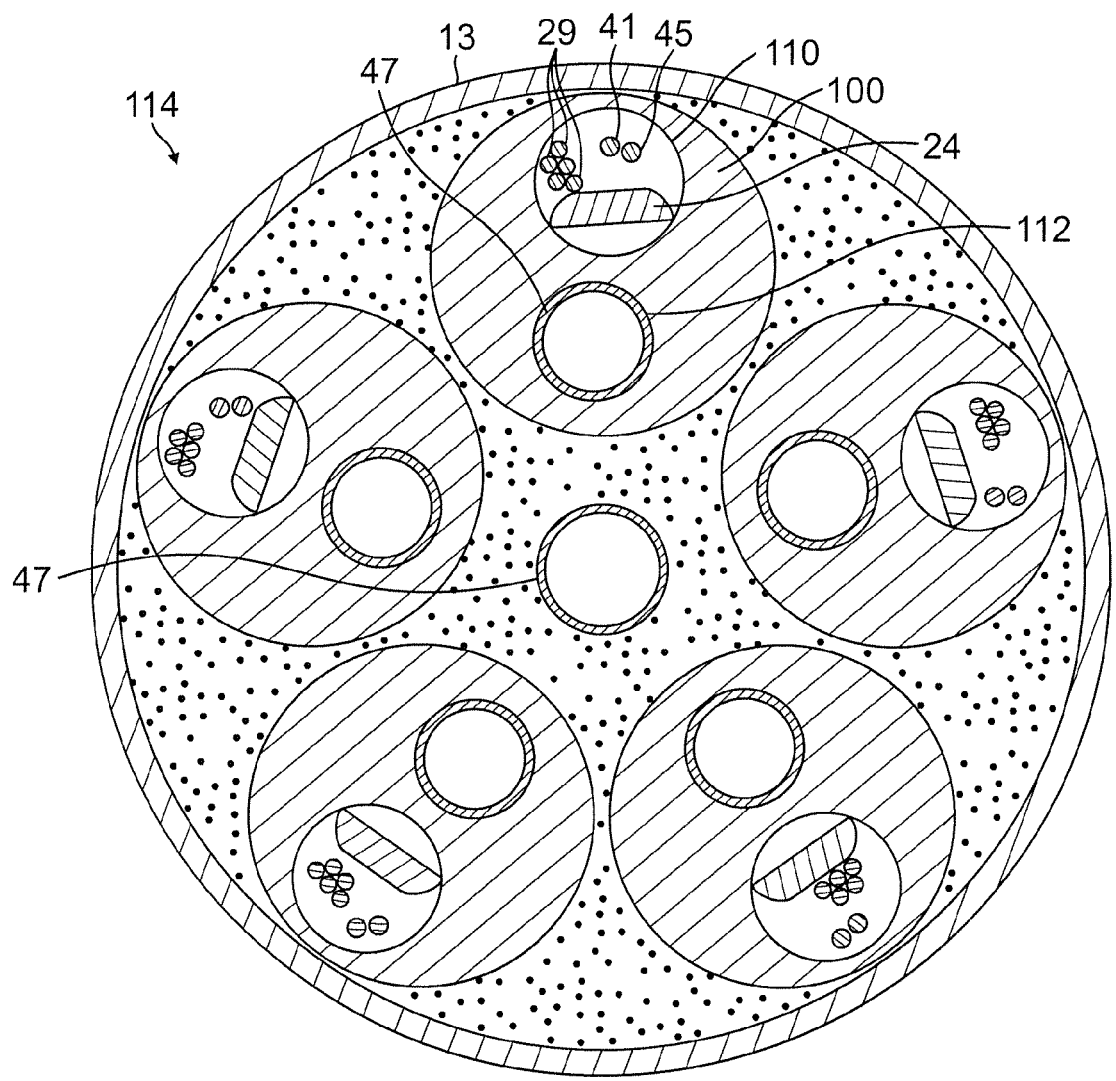
FIG. 8 is an end cross-sectional view of the junction of FIG. 7, taken along line 8-8.
Figure 9:
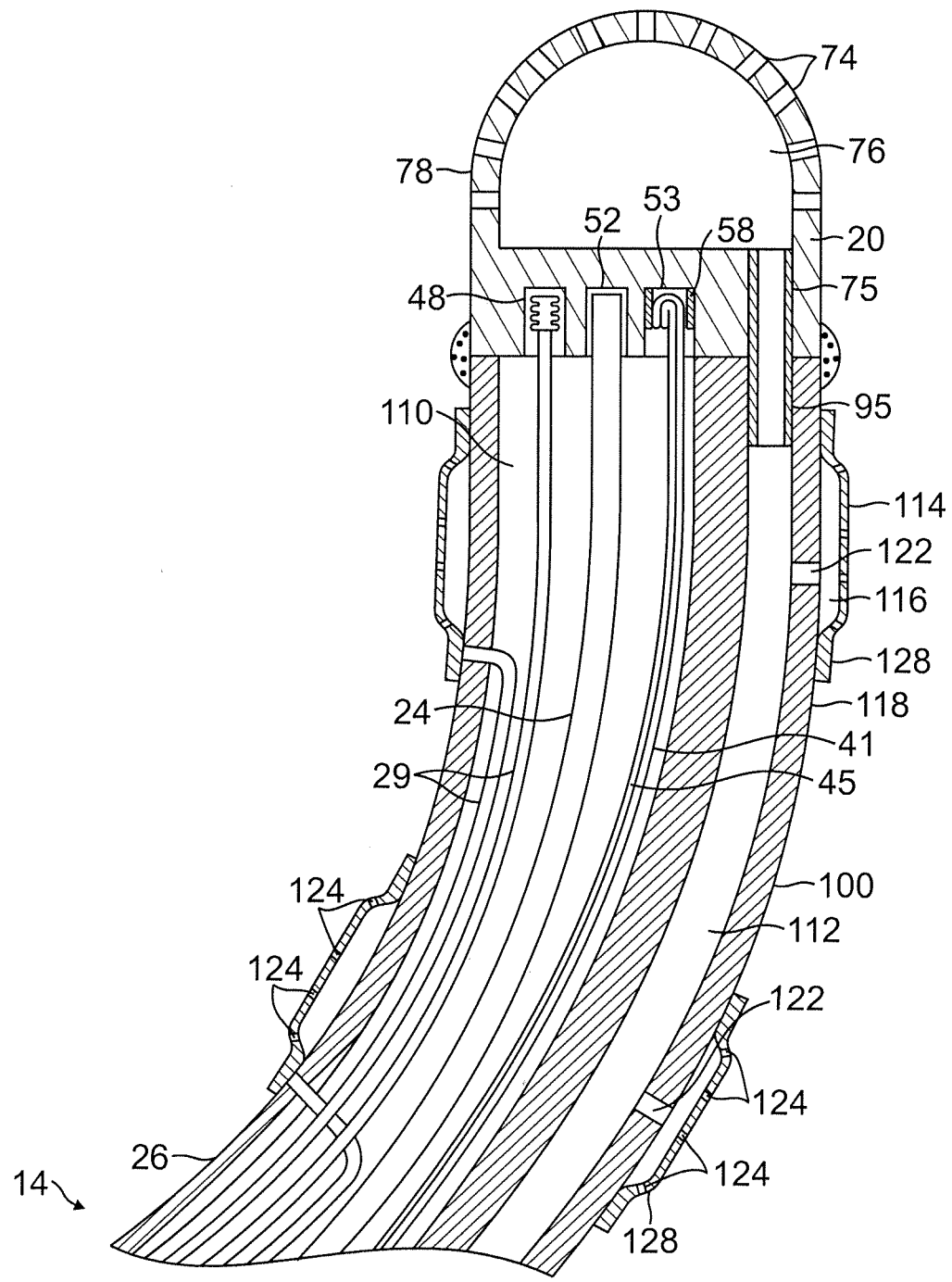
FIG. 9 is a side cross-sectional view of a portion of a spine in accordance another embodiment of the present invention.

An alternate embodiment is illustrated in FIGS. 7, 8 and 9 with each spine 114 comprising a multi-lumened tube 100 with at least two lumens, including a lumen 110 for the lead wires 29, thermocouple wires 41 and 45 and/or the support arm 24, and a lumen 112 for irrigation fluid. A plurality of short connector tubes 47 extend between the distal end of the main irrigation tube 44 and the proximal end of a respective spine irrigation lumen 112. The lumen 112 delivers irrigation fluid to irrigated ring electrodes 128, and to the tip electrode 20 via a short irrigation connector tube 95 that connects the irrigation passage 75 and the lumen 112. The irrigated ring electrodes 128 mounted on the tube can be adapted for mapping, sensing and/or ablation and are configured with a raised mid-portion 114 (FIG. 9) to form an annular fluid chamber 116 with an outer wall 118 of the tube 100. Fluid passes from the lumen 112 through a hole 122 formed in the outer wall 118 and is distributed in the annular fluid chamber 116 before exiting the electrodes 128 through apertures 124 formed in and near the raised mid-portion 114.

Figure 10:
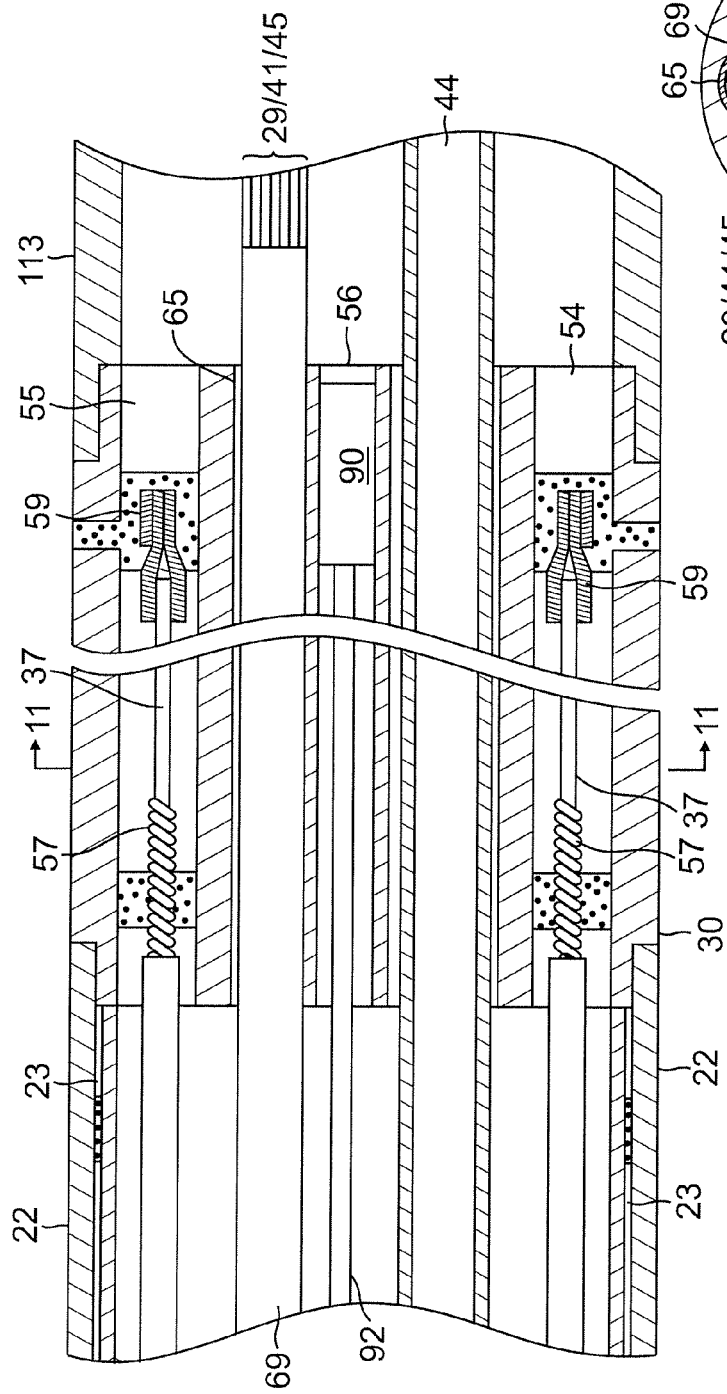
FIG. 10 is a side cross-sectional view of a portion of a catheter in accordance with yet another embodiment of the present invention, including an intermediate deflectable section.
Figure 11:
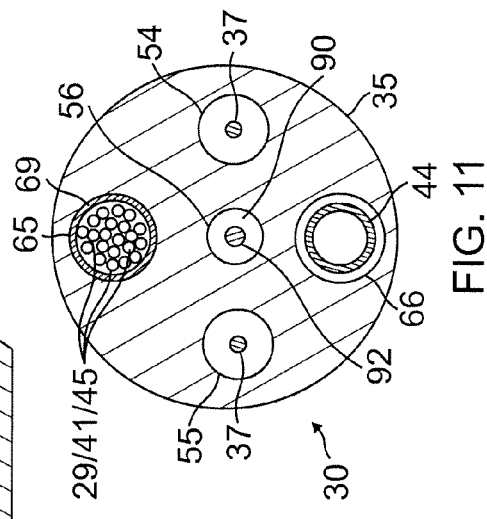
FIG. 11 is an end cross-sectional view of the intermediate deflectable section of FIG. 10, taken along line 11-11.

If desired, the catheter of the present invention may include a steering mechanism for deflection of the distal end of the catheter body 12. As illustrated in FIGS. 10 and 11, the catheter includes an intermediate deflectable section 30 extending between the catheter body 12 and the spines 14. The catheter body 12 of comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner.

The inner surface of the outer wall 22 is lined with a stiffening tube 23, which can be made of any suitable material, such as polyimide or nylon. The stiffening tube 23, along with the braided outer wall 22, provides improved torsional stability while at the same time minimizing the wall thickness of the catheter, thus maximizing the diameter of the central lumen 18. The outer diameter of the stiffening tube 23 is about the same as or slightly smaller than the inner diameter of the outer wall 22. Polyimide tubing may be used for the stiffening tube 23 because it may be very thin walled while still providing very good stiffness. This maximizes the diameter of the central lumen 18 without sacrificing strength and stiffness.

The intermediate deflectable section 30 comprises a short length of tubing 35, e.g., 2.0 to 4.0 inches in length, that is more flexible than the remainder of the catheter body 12. The tubing 35 is multi-lumened with lumens 54, 55, 56, 65 and 66. Extending through the lumen 65 are the lead wires 29 and thermocouple wires 41 and 45. A nonconductive protective sheath 69 may be provided to extend through the catheter body 12 and the intermediate deflectable section 30. Extending through the lumen 66 is the main irrigation tube 44.

A suitable steering mechanism comprises one, if not two, puller wires 37 that extend from a proximal end in the control handle 16, through the central lumen 15 in the catheter body 12 and into diametrically opposed, off-axis lumens 54 and 55 in the short length of tubing 35. Within the catheter body 12, each puller wire 37 extends through a respective closely wound compression coil 57 that is bendable but substantially non-compressible. The coils 57 have proximal and distal ends that are fixed near the proximal and distal ends, respectively, of the catheter body 12 to prevent deflection of the catheter body 12. The distal end of each puller 37 wire is anchored at the distal end of the short length of tubing in its respective off-axis lumen by means of a T-bar 59 (FIG. 10). As understood by one of ordinary skill in the art, the proximal end of each puller wire 37 is anchored to a movable member (e.g., a thumb control 85 of FIG. 1) in the handle 16 that can be moved relative to the catheter body 12. Proximal movement of the movable member relative to the catheter body 12 results in deflection of the short length of tubing to one side or another, generally within a plane, depending on the puller wire actuated. An example of such a steering mechanism and construction is described in more detail in U.S. Pat. No. 6,064,905, the disclosure of which is incorporated herein by reference.

It may also be desirable for the catheter of the present invention to include a location sensor, especially where the catheter includes a steering mechanism. In the depicted embodiment of FIGS. 10 and 11, the tube 35 of the intermediate deflectable section 30 has a dedicated lumen 56 for location sensor 90 and sensor cable 92. The location sensor 90 is positioned at or near the distal end of the tube 35 and is used to determine the coordinates of the distal assembly 18, for example, at each instant when the electrodes 20 and 28 are being used to collect electrical mapping data points and electrical activity data (e.g., ECG) and/or to ablate.

The sensor cable 92 extends through the lumen 56 of the intermediate section 30, the central lumen 15 of the catheter body 12, the control handle 16 and out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 92 comprises multiple wires encased within a plastic covered sheath. In the sensor control module, the wires of the sensor cable 92 are connected to the circuit board. The circuit board amplifies the signal received from the corresponding location sensor 90 and transmits it to a computer in a form understandable by the computer by means of a sensor connector at the proximal end of the sensor control module.

The location sensor 90 may be an electromagnetic location sensor. For example, the location sensor 90 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 90 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. Other suitable location sensors 90 are single axis sensors, such as that described in the U.S. patent application Ser. No. 09/882,125 filed Jun. 15, 2001, entitled "Position Sensor Having Core with High Permeability Material," the disclosure of which is incorporated therein by reference, and in U.S. patent application Ser. No. 12/982,765 filed Dec. 30, 2010, entitled "Catheter with Single Axial Sensors," the disclosure of which is incorporated herein by reference.

Alternatively or in addition to the foregoing single location sensor 90, a location sensor may be mounted on each spine, for example, at or near the tip electrode 20. Smaller sensors are particularly desirable for that purpose because of the need to keep the diameters of the spines 14 small enough so that they all fit within the lumen of a guiding sheath.

Distal of the intermediate deflectable section 30 is a short connector tubing 113 has that is comparable in structure and design to the aforementioned tubing 13 of the catheter body 12 of FIG. 2 or FIG. 7. It is understood that the distal end of the connector tubing 113 can be structured similarly to the distal end of the tubing 13 of FIG. 2 or FIG. 7 so as to allow mounting of the proximal ends of the spines 14 in construction of the distal assembly 18 by means of the mounting assembly 31.

To use the catheter 10 of the invention, a cardiologist or electrophysiologist introduces a guiding sheath and a dilator into the patient, as is generally known in the art, so that the distal ends of the sheath and dilator are in the region of the heart to be mapped. Thereafter, the dilator is removed from the guiding sheath, and the catheter 10 is introduced into the patient through the guiding sheath. To insert the catheter 10 into the guiding sheath, the mapping assembly 18 must be in its collapsed arrangement, wherein each spine 14 is disposed generally along the longitudinal axis of the catheter body 12. A suitable guiding sheath for use in connection with the catheter 10 is the PREFACE™ Braided Guiding Sheath (commercially available from Biosense Webster, Inc., Diamond Bar, Calif.). Such a guiding sheath has sufficient strength to hold each support arm 24 in the collapsed arrangement, such that the spines 14 and also the entire remainder of the catheter 10 can travel within the guiding sheath, from an insertion point in the patient, through a vein or artery and to a desired location in the heart.

Once the distal end of the catheter has reached the desired location, such as a position within the left ventricle of the heart, relative longitudinal movement between the catheter 10 and the guiding sheath is provided to allow at least a portion of each spine 14 to protrude from the guiding sheath. Preferably the guiding sheath is moved proximally relative to the distal end of the catheter to expose the spines 14. When a portion of each spine 14 protrudes from the guiding sheath and a compression force is no longer applied by the guiding sheath on the spines, the shape memory of the support arms 24 allows the support arms to revert to an expanded arrangement. The distal assembly 18 can be advanced into a tubular structure off the left ventricle, such as a pulmonary vein, as illustrated in FIG. 6A. With the distal assembly in the expanded arrangement of FIG. 6B, at least one electrode from each spine 14 can be placed into contact with the heart tissue at a plurality of locations such that electrical, locational and mechanical information can be obtained from such locations of the tissue for generating a 3-D map of the tissue. Additionally, with the electrodes 20 and 28 in contact with heart tissue, either the tip electrodes or selected ring electrodes can be energized for ablation in creating a lesion isolation line along the circumference of the energized electrodes. In that regard, the catheter can be rotated along its longitudinal axis (e.g., by rotating the control handle along its longitudinal axis) so that the electrodes 20 and 28 are repositioned to ablate different locations along the circumferences to create a generally continuous isolation line. And because the tip and ring electrodes are in contact with the heart tissue along different circumferences generally parallel with the ablated circumference, any of the electrodes in the other circumferences can be used to sense electrical activity at such adjacent circumferences in detecting errant electrical activity that may indicate gaps in the lesion isolation line. Such sensing can advantageously be conducted during or between ablation without the use of another catheter or the need to reposition the catheter. After mapping and ablation are completed, the catheter is moved proximally relative to the guiding sheath to retract the spines within the sheath.

During mapping and ablation, the region between the spines 14 and at the electrodes 20 and 28 can be prone to thrombus formation and/or overheating. Accordingly, irrigation fluid is introduced through the irrigation tube 44 before, during and/or after a mapping and ablation procedure to flush the region between the spines 14 and the electrodes. Preferably irrigation is provided continuously during the procedure to minimize any potential blood clotting in the irrigation tube. Suitable irrigation fluids for use in connection with the invention include saline, heparinized saline and thrombolitica. Although the irrigation tube 44 is preferably positioned coaxial with the catheter body 12 so that it is mounted between all of the spines, other positions for the irrigation tube at or near the distal end of the catheter can be used in accordance with the present invention.

The expanded arrangement of spines 14 in a neutral state can take on various shapes. In an alternate embodiment as shown in FIG. 12, a distal assembly 18' has spines 14', each with a generally straight proximal portion 60', and a nonlinear or curved distal portion 64' that extends radially outwardly from the catheter body 12. The spines 14' also assume a generally U-shaped configuration when the distal assembly 18' is advanced into a tubular region.

Figure 13B:
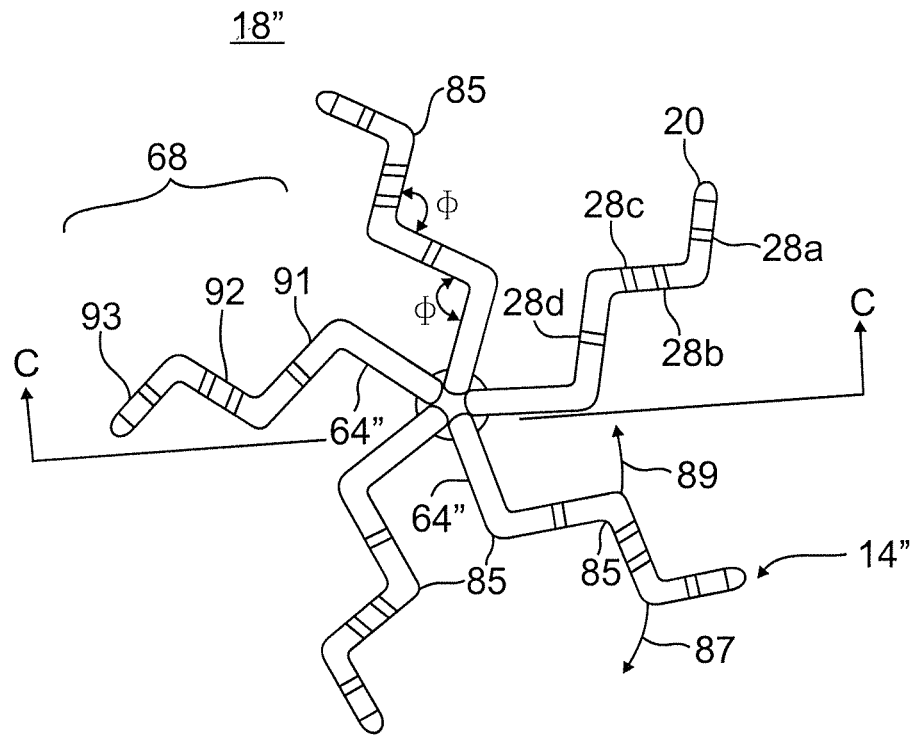
FIG. 13B is a top plan view of the distal assembly of FIG. 13A.
Figure 13C:
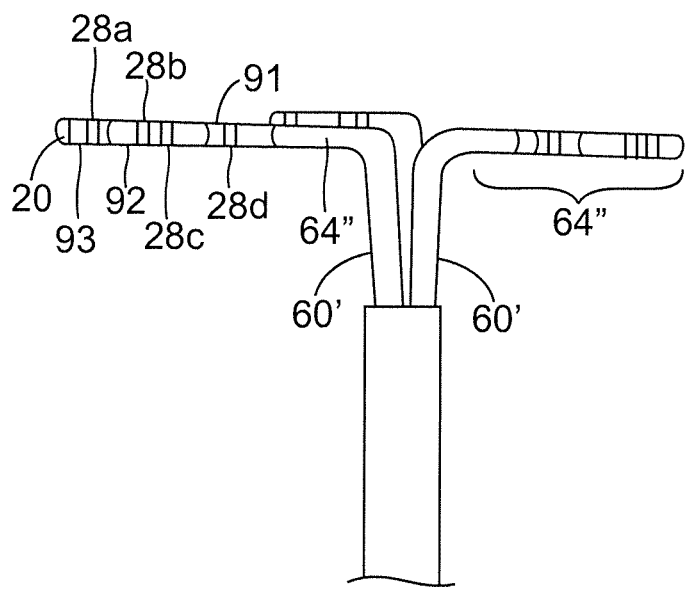
FIG. 13C is a side view of the distal assembly of FIG. 13B, taken along line C-C.
Figure 13D:
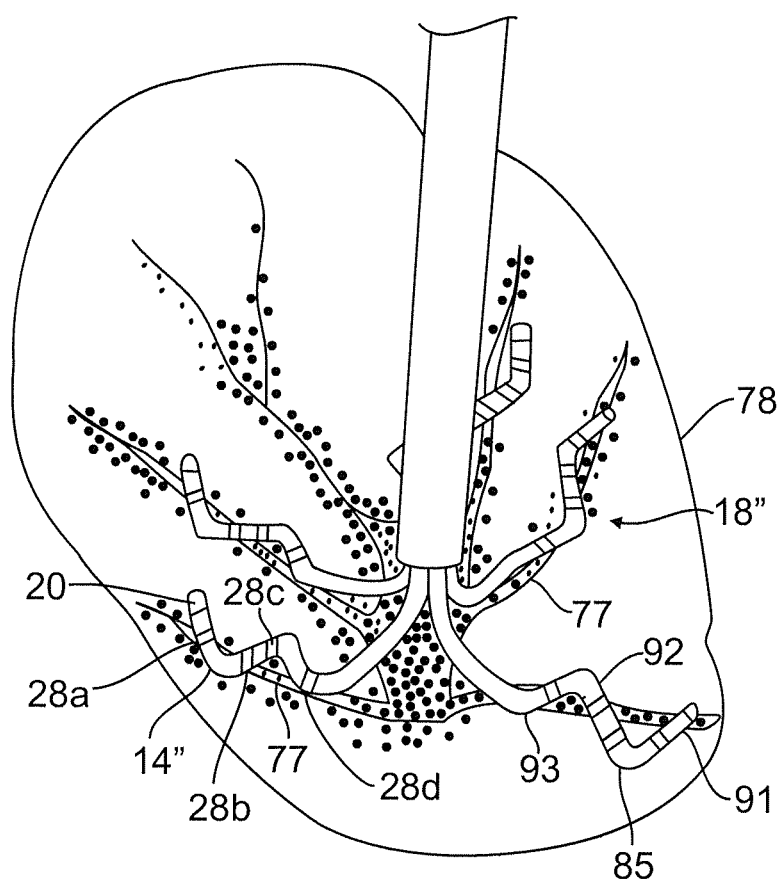
FIG. 13D is a perspective view of the distal assembly of FIG. 13A in a tubular region.

In yet another embodiment as shown in FIG. 13A, a distal assembly 18" has spines 14", each with a generally straight proximal portion 60", and a distal portion 64" having a zig-zag portion 68 that includes at least two generally straight sections that are angularly offset from adjacent sections at angles φ of between about 45 to 90 degrees. In the illustrated embodiment, there are three sections: a proximal section 91 with ring electrode 28d, a middle section 92 with ring electrodes 28b and 28c, and a distal section 93 with ring electrode 28a and tip electrode 20. As illustrated in FIG. 13B, the spines 14" advantageously form a "pinwheel" pattern such that corners 85 (defined by offset angles φ) of the spines point clockwise (arrow 87) or counterclockwise (arrow 89) when the distal assembly 18" (especially when the spines are in a neutral state) is viewed on-axis. In contrast, when the distal assembly is viewed from the side as illustrated in FIG. 13C (with spines in an neutral state), each spine 14" generally lies within a plane. With the "pinwheel" zig-zag configuration, the spines 14" are less prone to slide into radial grooves 77 of a tubular region 78 and are more prone to lie flat against the tissue, as illustrated in FIG. 13D.

Using the inventive catheter 10 having multiple spines 14, each having electrical and mechanical mapping and ablation capabilities, the cardiologist can map local activation time and obtain voltage maps, and ablate in a circumferential manner to create an ablation isolation line in a tubular region of the heart. The cardiologist can ablate at a first circumference with the tip electrodes while obtaining an electrocardiogram with the ring electrodes at adjacent circumferences to detect any gaps in the ablation isolation line at the first circumference during or between ablation without the need for a second catheter or repositioning of the ablation catheter, which lessens the cost and duration of the procedure.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. As also understood by one of ordinary skill in the art, the drawings are not necessarily to scale. Accordingly, the foregoing description should not be read as pertaining only to the precise structures described and shown in the accompanying drawings, but rather should be read as consistent with and as support for the following claims, which are to have their fullest and fairest scope.

The invention claimed is:

1. A catheter adapted for use in a tubular structure at or near a heart, comprising:

an elongated catheter body having a proximal end, a distal end and at least one lumen extending longitudinally therethrough;

a distal assembly distal of the catheter body and comprising at least two spines, each spine having a free distal end and a proximal end that is affixed to the catheter body, wherein each spine comprises a distal tip electrode, at least one ring electrode and a dedicated irrigation pathway, at least one of the distal tip electrode and the at least one ring electrode being adapted for irrigation;

a main irrigation pathway extending through the catheter body and being adapted to introduce irrigation fluid to outside the catheter in a region between the spines; and wherein each spine has a support arm adapted to support the spine in a generally L-shaped configuration such that the free distal end of each spine is positioned radially outwardly from the proximal end when the spine is in a neutral state, and in a generally U-shaped configuration such that the tip electrode and the at least one ring electrode of each spine are simultaneously in contact with tissue of the tubular structure upon exertion of a contact force on the distal assembly by the tubular structure, wherein in the U-shaped configuration the distal tip electrode of each spine defines an angle with the proximal end of the corresponding spine of about 90 degrees to about 135 degrees.

2. The catheter of claim 1, wherein the tip electrode of each spine is configured to contact the tissue of the tubular structure along a first common circumference and the at least one ring electrode of each spine contacts the tissue of the tubular structure along a second common circumference.

3. The catheter of claim 2, wherein the second common circumference is configured to be positioned deeper in the tubular structure than the first common circumference.

4. The catheter of claim 1, wherein each spine comprises a common plurality of ring electrodes.

5. The catheter of claim 1, wherein the tip electrode of each spine is adapted for ablation.

6. The catheter of claim 1, wherein the at least one ring electrode of each spine is adapted for sensing electrical activity in the tubular structure.

7. The catheter of claim 1, wherein the at least one ring electrode is adapted for ablation.

8. The catheter of claim 1, wherein the tip electrode is adapted for sensing electrical activity in the tubular structure.

9. The catheter of claim 1, wherein the support arm has shape memory.

10. The catheter of claim 1, further comprising a spine mounting assembly adapted to secure the proximal ends of the spines to the catheter body.

11. The catheter of claim 1, wherein each spine has a distal portion and a proximal portion.

12. The catheter of claim 11, wherein the proximal portion includes generally straight sections angularly offset from each other.

13. The catheter of claim 1, wherein the distal assembly comprises about five spines.

14. The catheter of claim 11, wherein the distal portion includes a zig-zag portion.

15. The catheter of claim 1, wherein the distal assembly has a pinwheel pattern.

16. The catheter of claim 1, wherein the distal assembly is moveable between an expanded arrangement, in which each spine extends radially outward from the catheter body, and a collapsed arrangement, in which each spine is disposed generally along a longitudinal axis of the catheter body.

17. The catheter of claim 1, wherein each spine has a proximal portion and a distal portion generally orthogonal to the proximal portion when the spine is in a neutral state.

18. The catheter of claim 1, wherein the tip electrode is adapted for irrigation.

19. The catheter of claim 1, wherein the at least one ring electrode is adapted for irrigation.

20. A method for ablating a tubular structure of the heart comprising:
    introducing the distal assembly of the catheter of claim 1 into the tubular structure;
    positioning the distal assembly so that the tip electrode and the at least one ring electrode from each spine are simultaneously in contact with tissue;
    energizing one of the tip electrode and the at least one ring electrode to ablate the tissue along a first circumference;
    sensing electrical activity of the tissue at the other of the tip electrode and the at least one ring electrode along a second circumference.

21. A method of claim 20, wherein the sensing electrical activity occurs without repositioning of the distal assembly after the energizing the one of the tip electrode and the at least one ring electrode.

* * * * *